(12) United States Patent
Declercq et al.

(10) Patent No.: US 8,465,973 B2
(45) Date of Patent: Jun. 18, 2013

(54) TOPICAL COMPOSITIONS CONTAINING PHOSPHORYLATED POLYPHENOLS

(75) Inventors: Lieve Declercq, Ekeren (BE); Hugo Corstjens, Maaseik (BE); Daniël Maes, Huntington, NY (US); Willy Van Brussel, Ghent (BE); Geert Schelkens, Wetteren (BE)

(73) Assignees: Estee Lauder Coordination Center N.V., Devel (BE); Ajinomoto Omnichem S.A., Mont-Saint-Guibert (BE)

( * ) Notice: Subject to any disclaimer, the term of this patent is extended or adjusted under 35 U.S.C. 154(b) by 0 days.

(21) Appl. No.: 12/481,156

(22) Filed: Jun. 9, 2009

(65) Prior Publication Data

US 2009/0247490 A1 Oct. 1, 2009

Related U.S. Application Data

(62) Division of application No. 11/574,252, filed as application No. PCT/BE2004/000132 on Sep. 14, 2004.

(51) Int. Cl.
*C12N 5/00* (2006.01)

(52) U.S. Cl.
USPC .......................................................... 435/375

(58) Field of Classification Search
None
See application file for complete search history.

(56) References Cited

U.S. PATENT DOCUMENTS

| | | | |
|---|---|---|---|
| 4,617,293 A | 10/1986 | Wahlig et al. | |
| 4,698,360 A | 10/1987 | Masquelier | |
| 4,963,527 A | 10/1990 | Bombardelli et al. | |
| 5,925,621 A | 7/1999 | Zaneveld et al. | |
| 6,008,260 A | 12/1999 | Pezzuto et al. | |
| 6,132,740 A | 10/2000 | Hu | |
| 6,147,121 A | 11/2000 | Breton et al. | |
| 6,180,662 B1 | 1/2001 | Lanzendörfer et al. | |
| 6,270,780 B1 | 8/2001 | Carson et al. | |
| 6,437,004 B1 | 8/2002 | Perricone | |
| 6,544,581 B1 | 4/2003 | Shrikhande et al. | |
| 6,696,495 B2 | 2/2004 | Mueller | |
| 2002/0016998 A1 | 2/2002 | Pruche et al. | |
| 2004/0116386 A1* | 6/2004 | Pifferi et al. | 514/78 |
| 2005/0080024 A1* | 4/2005 | Tucker et al. | 514/27 |
| 2008/0076833 A1 | 3/2008 | Van Brussel et al. | |

FOREIGN PATENT DOCUMENTS

| | | |
|---|---|---|
| DE | 3942688 A1 | 6/1991 |
| EP | 0543555 | 5/1993 |
| EP | 0904774 A1 | 3/1999 |
| EP | 0953345 A1 | 11/1999 |
| EP | 1013260 | 6/2000 |
| EP | 1058864 | 12/2000 |
| EP | 1138323 A2 | 10/2001 |
| JP | 09194493 A * | 7/1997 |
| JP | 9194493 A | 7/1997 |
| JP | 2002-306126 A | 10/2002 |
| WO | WO99/04747 | 2/1999 |
| WO | WO99/44099 | 9/1999 |
| WO | WO0130336 A2 | 5/2001 |
| WO | WO03/086414 A1 | 10/2003 |
| WO | WO2004/054533 A1 | 7/2004 |
| WO | WO2006/078941 | 7/2006 |

OTHER PUBLICATIONS

PCT International Search Report; International Application No. PCT/BE2004/000132; Completion Date: May 10, 2005; Date of Mailing: May 24, 2005.
PCT Written Opinion of the International Searching Authority, or the Declaration; Completion Date: May 10, 2005 ; Date of Mailing: May 24, 2005.
Ragione, et al., "Antioxidants induce different phenotypes by a distinct modulation of signal transduction;" Febs Letters 26789; Elsevier Science Publishers; Amsterdam, NL; vol. 532; No. 3; pp. 289-294; Dec. 2002.

* cited by examiner

*Primary Examiner* — Qiuwen Mi
(74) *Attorney, Agent, or Firm* — Idris N. McKelvey

(57) ABSTRACT

The present invention provides topical compositions containing phosphorylated polyphenols in combination with a topically acceptable carrier. The compositions of the invention provide a means for delayed delivery of the polyphenol to keratinous tissues, such as skin, hair and nails, with enzymes of the keratinous tissue dephosphorylating the polyphenol, and returning it to its native active form. The compositions are particularly useful in the regulation of skin conditions. the phosphorylated stilbene is a phosphorylated resveratrol or a phosphorylated resveratrol derivative.

10 Claims, 3 Drawing Sheets

TOPICAL COMPOSITIONS CONTAINING PHOSPHORYLATED POLYPHENOLS

This is a divisional of U.S. patent application Ser. No. 11/574,252 filed Feb. 26, 2007, now abandoned which claims priority to International Patent Application No. PCT/BE2004/000132 filed Sep. 14, 2004.

FIELD OF THE INVENTION

The invention relates to compositions for application to the skin. In particular, the invention relates to topical compositions containing stabilized polyphenol compounds.

BACKGROUND OF THE INVENTION

The group of compounds known as polyphenols exhibit a wide variety of biological activities, and are widely used in topical formulations for treatment of the skin. One particularly widely exploited function of many polyphenols is as antioxidants. In this role, these compounds can serve two roles: they can protect the compositions in which they are delivered from oxidative degradation, as well as providing protection to the akin to which they are applied from the ravages of free radicals. Ironically, however, these protective molecules themselves are susceptible to damage from external sources. These versa-tile compounds are highly susceptible to degradation by exposure to heat or light, frequently resulting in discoloration of the composition in which they are contained, as well as diminishing their efficacy when applied to the skin. Because of this weakness, the true scope of their utility has not yet fully been realized. Compositions containing unprotected polyphenols are not likely to deliver their complete biological potential, and the provision of protective packaging or special handling necessary to preserve their activity is too costly to be commercially feasible on a large scale. Thus, there continues to be a need for polyphenol-containing compositions with improved stability and retained biological activity.

SUMMARY OF THE INVENTION

The present invention provides topical compositions comprising at least one phosphorylated polyphenol and a topically acceptable carrier; these compositions provide a greater stability of biological activity as well as compositional integrity than is possible with an unmodified polyphenol. The compositions of the invention are particularly useful in, among other uses, methods for scavenging free radicals on the skin, and treating and reducing the symptoms of aging on the skin. The invention also provides a method of delayed release of polyphenols on the skin which comprises applying to the skin a composition containing at least one phosphorylated polyphenol and a topically acceptable carrier. The invention also provides a method for rendering water-soluble an insoluble polyphenol which comprises phosphorylating the insoluble polyphenol to an extent sufficient to render the polyphenol water-soluble.

SHORT DESCRIPTION OF THE DRAWINGS

Figure 1:
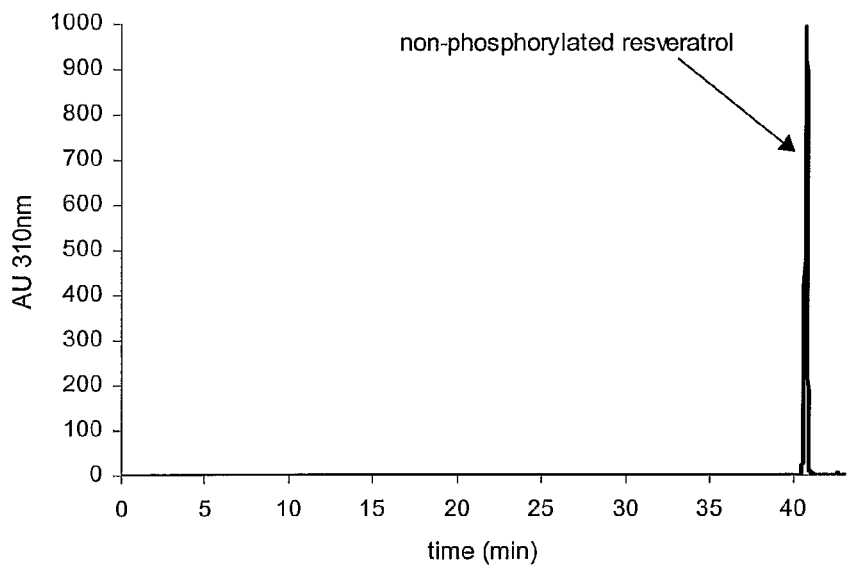
Figure 1:
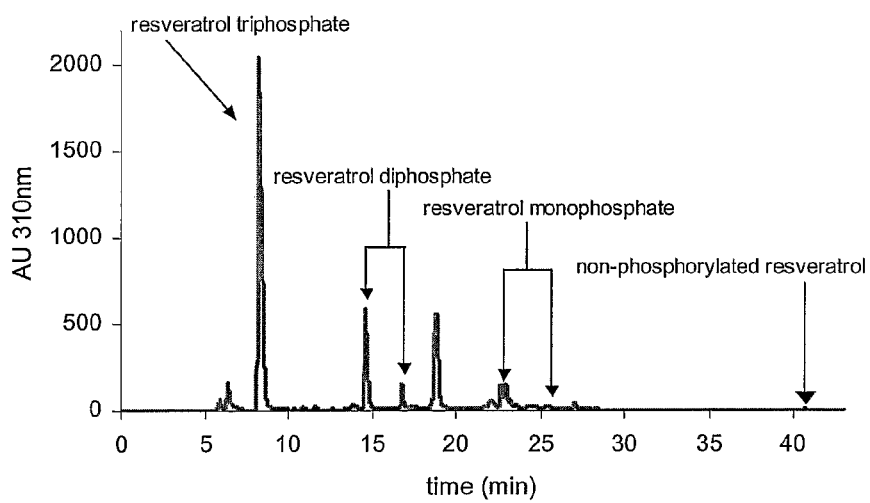

FIG. 1. HPLC analysis of resveratrol: non-phosphorylated starting material in upper frame and highly phosphorylated resveratrol in lower frame.

Figure 2:
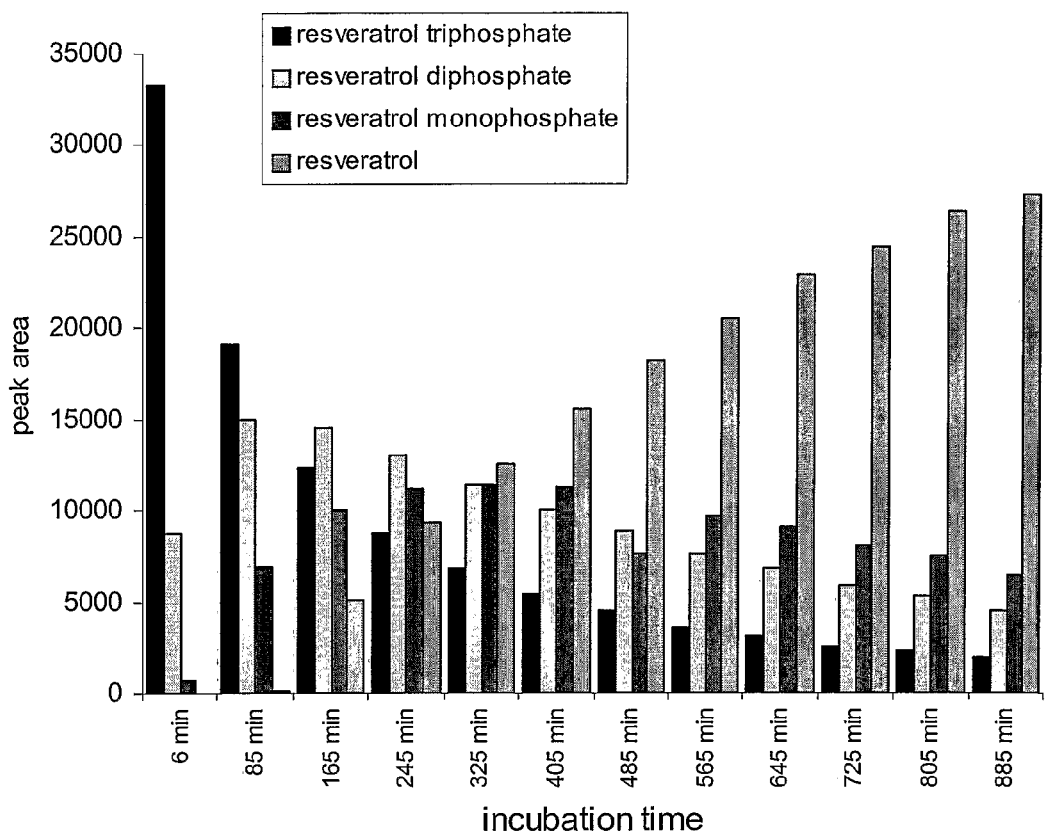

FIG. 2. Time dependent formation of resveratrol from phosphorylated resveratrol upon incubation with acid phosphatase from wheat germ.

Figure 3:
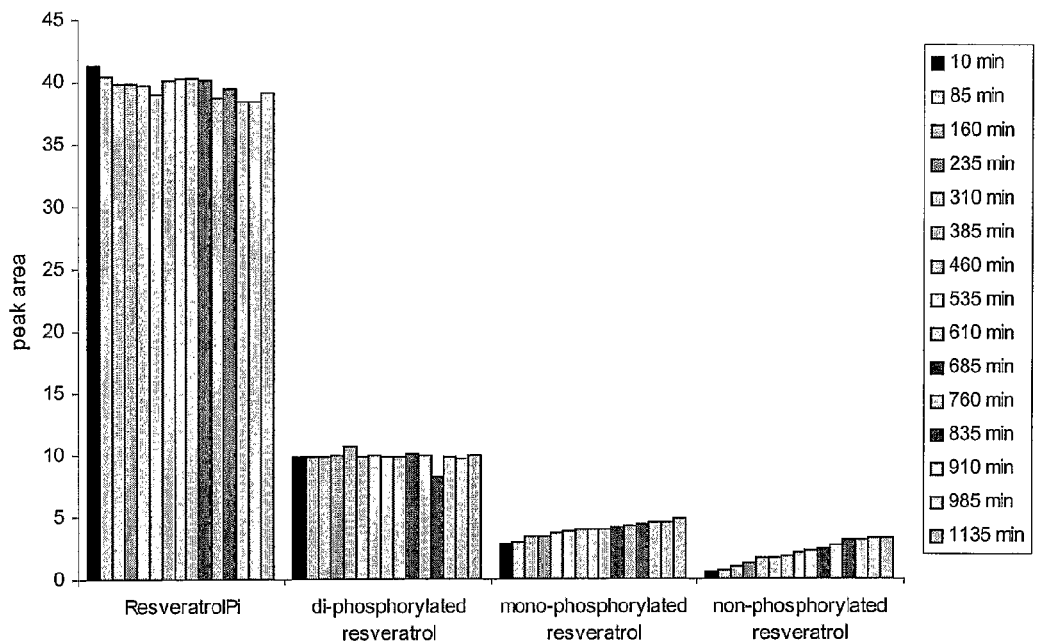

FIG. 3 Time dependent formation of resveratrol from phosphorylated resveratrol upon incubation with the extractable fraction of human SC D-squame tape strippings.

Figure 4:
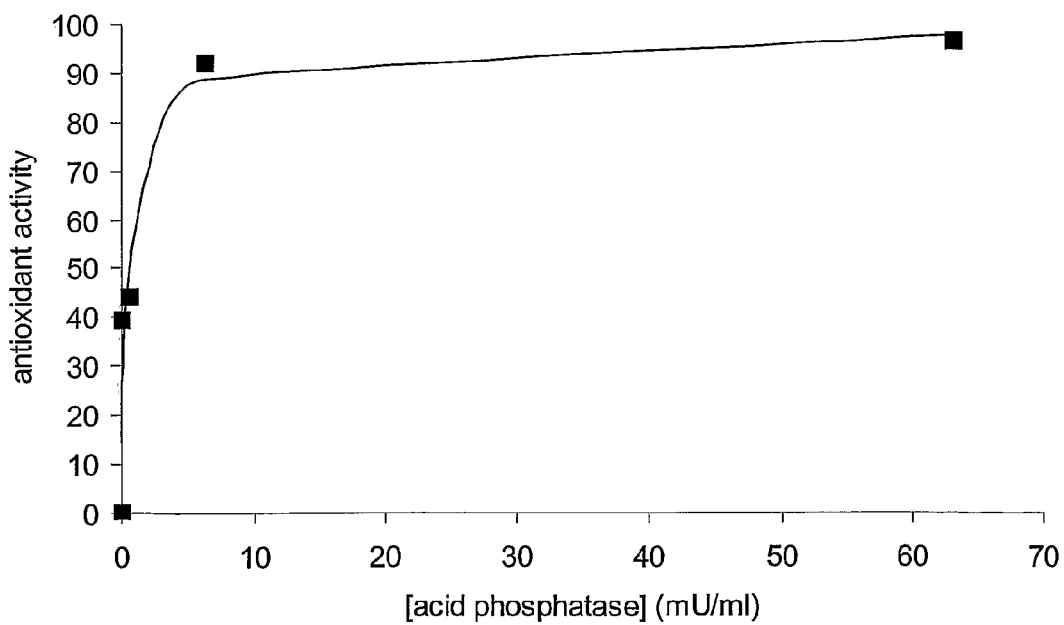

FIG. 4 Restoration of in vitro antioxidant activity of phosphorylated resveratrol upon incubation with increasing concentrations of acid phosphatase from wheat germ.

DETAILED DESCRIPTION OF THE INVENTION

The compositions of the invention utilize phosphate esters of polyphenols as an active component. The active components are polyphenol molecules that have been stabilized by the phosphorylation of one or more hydroxyl groups on the molecule. While the phosphorylation of the molecule results a reduction in the susceptibility to degradation, the modified compounds retain the innate biological activity of the unmodified polyphenol molecule upon removal of the phosphate groups. In one embodiment, the compositions of the invention comprise phosphate esters of polyphenols represented by the formulas $ROP(O)(OH)_2$, $ROP(O)(OH)OP(O)(OH)_2$, or $ROP(O)(OH)OP(O)(OH)OP(O)(OH)_2$ and/or a metal salt of one of these; with R representing an organic polyphenolic molecule which may be modified to contain one or more phosphate ester groups.

The polyphenols employed in the compositions can be any that are cosmetically or pharmaceutically acceptable for topical application to mammalian skin. By "cosmetically or pharmaceutically acceptable" is meant compounds that can be used in safe and effective amounts on mammalian skin, hair or nails, preferably on human skin, hair or nails. Biologically active polyphenols are widely known, and are readily found in natural sources, such as various plant extracts. The polyphenols useful in the compositions of the invention will be understood to encompass naturally occurring polyphenols, synthetic derivatives of polyphenols, as well as plant extracts containing at least one polyphenolic component.

In one embodiment of the invention, the polyphenol to be phosphorylated is as simple compound having one aromatic ring with at least one hydroxyl group. Such compounds have the generic formula:

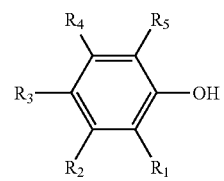

wherein $R_1$, $R_2$, $R_3$, $R_4$, $R_5$ each independently of each other is hydrogen, hydroxide, carboxyl, Z, OZ or COOZ, preferably where at least one of the substituents $R_1$, $R_2$, $R_3$, $R_4$, $R_5$ is a hydroxyl or carboxyl group, Z being an alkyl chain consisting of 1-10 carbon atoms or being CHCHCOOY with Y=hydrogen or an alkyl chain of 1-4 carbon atoms. Preferably, more than one of the R substituents is a hydroxyl group. Typical compounds in this group include catechol, pyrogallol, guaiacol, and resorcinol, with two hydroxyl groups; pyrogallol and hydroxyacids and their esters, such as gallic acid, methyl gallate, ethyl gallate, propyl gallate and octyl gallate with three hydroxyl groups; salicylic acid, with one hydroxyl group and a carboxyl group; and hydroxycinnamic acids and esters, where one R group is a vinylic acid or ester, such as p-coumaric acid, caffeic acid, ferulic acid, sinaptic acid, chlorogenic acid, curcumins and analogues in which the carboxylic acid group is esterified with a simple C1-C10 alcohol.

In a preferred embodiment, however, the topically useful polyphenols to be phosphorylated are more complex molecules selected from the group of compounds known generically as tannins. Tannins comprise two main groups, condensed tannins and hydrolysable tannins. The phosphorylated tannins of the invention can be generically represented by the generic formulas $ArOP(O)(OH)_2$ product, an $ArOP(O)(OH)OP(O)(OH)_2$, or an $ArOP(O)(OH)OP(O)(OH)OP(O)(OH)_2$ product and/or a metal salt of one of these, wherein Ar represents a condensed or a hydrolysable tannin. Both hydrolysable and condensed tannins and examples thereof are well described in the standard work "Chemistry of vegetable tannins" by E. Haslam, Ed. Academic Press, London, 1966, the contents of which are incorporated herein by reference. Condensed tannins are composed of phenolic derivatives that are part of a larger structure with at least two aromatic rings, and which cannot be completely hydrolysed, as at least one phenolic ring is attached by at least one carbon-carbon bond (single or double) or an ether linkage to another part of the molecule. The condensed tannin may be a condensed tannin represented by or corresponding to the general formula:

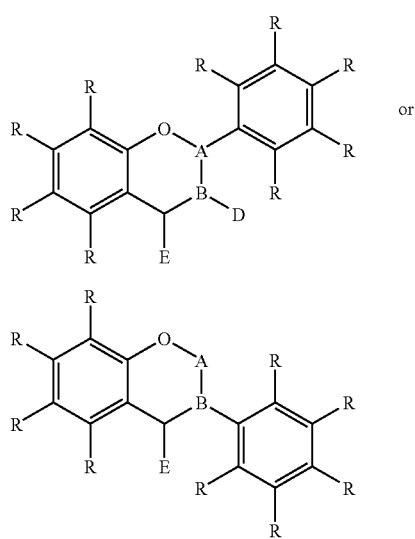

wherein:
  A and B are carbon atoms connected by a single or by a double bond
  D is hydrogen, hydroxide, or a hydroxide esterified with gallic acid or ellagic acid
  E is hydrogen, hydroxide, O-glucose or another condensed tannin corresponding to Formula (I) or (II)
  R is hydrogen, hydroxide, O-glucose, an O-alkyl group containing 1-3 carbon atoms or a phosphate group selected from the group consisting of $OP(O)(OH)_2$, $OP(O)(OH)OP(O)(OH)_2$, $OP(O)(OH)OP(O)(OH)OP(O)(OH)_2$ and a metal salt of such phosphate groups, with at least one of R being a phosphate group.

Typical product categories are flavonoids, stilbenes and phloroglucinols, each group of which contains topically useful polyphenols.

In one preferred embodiment, the condensed tannin is a flavonoid. A flavonoid can be defined as a compound with a structure the general formulas (I) or (II):

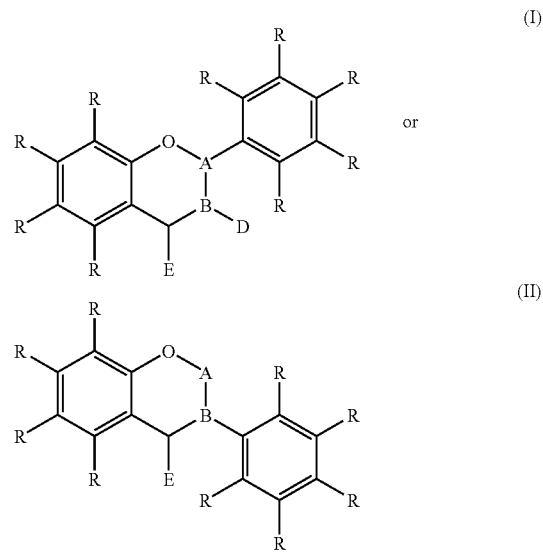

wherein:
  A and B are carbon atoms connected by a single or by a double bond
  D is hydrogen, hydroxide, or a hydroxide esterified with gallic acid or ellagic acid
  E is hydrogen, hydroxide, O-glucose or another phosphorylated flavonoid corresponding to Formula (I) or (II)
  R is hydrogen, hydroxide, O-glucose, an O-alkyl group containing 1-3 carbon atoms or a phosphate group selected from the group consisting of $OP(O)(OH)_2$, $OP(O)(OH)OP(O)(OH)_2$, $OP(O)(OH)OP(O)(OH)OP(O)(OH)_2$ and a metal salt of such phosphate groups, with at least one of R being a phosphate group.

Flavanols, flavonols, flavones, flavanones, isoflavanes, isoflavones all belong to the category of flavonoids as defined above. These terms are well known to the skilled practitioner (see e.g. Peterson et al. (1998), *J Am Diet Assoc* 98:682-5), and have a broad range of utility in topical application. Such flavonoids can occur in natural products, such as plant extracts, as much more complicated structures, for example as dimers or oligomers of the general structure defined above, or as even more complex derivatives thereof.

Certain preferred compounds in the category of phosphorylated condensed tannins are compounds according to Formula (III)

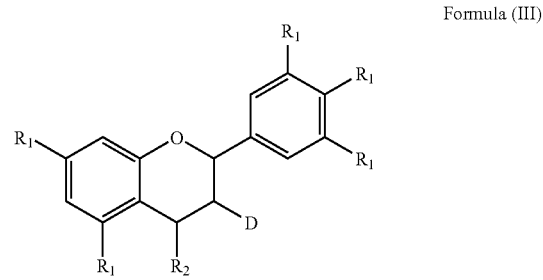

Formula (III)

wherein:
R₁ is hydrogen, hydroxide, O-glucose, an O-alkyl group containing 1-3 carbon atoms or a phosphate group selected from the group consisting of OP(O)(OH)₂, OP(O)(OH)OP(O)(OH)₂, OP(O)(OH)OP(O)(OH)OP(O)(OH)₂ and a metal salt of such phosphate groups, with at least one of R being a phosphate group.

D is hydroxide, O-glucose or a galloyl residue with 0-3 phosphate groups as defined for R₁

R₂ is a hydrogen or another component of Formula (III)

Typical product categories according to this formula are flavanoles and flavan-3,4-diols.

A more comprehensive listing of useful polyphenols for phosphorylation is provided below. In brief, typical examples of flavanols are catechine, epicatechine, dimers of catechine or epicatechine, oligomers and polymers of catechine or epicatechine where the monomers are connected via a C—C bond. The oligomers are known as proanthocyanidines, the polymers as condensed tannins. Further groups of compounds belonging to this category are cyanidins, anthocyanidins and procyanidins. Typical examples of flavonols are quercetine, kaempferol or myricetine.

Another group of condensed tannins containing compounds having topical utility are stilbene derivatives possessing phenolic hydroxyl functions. Typical examples thereof are the isomers of resveratrol. Yet another group of condensed tannins are the phloroglucinols, consisting of pyrogallol dimers, oligomers and polymers, where the pyrogallol moieties are connected via ether bonds or via C—C bonds between two aromatic carbon atoms. All these compounds defined as condensed tannins may be further esterified with acids such as ellagic acid or with gallic acid. Ellagic acid itself can also be considered as a condensed tannin.

Examples of natural extracts containing one or more types of condensed tannins include tannin extracts from trees such as *Eucalyptus* sp., *Acacia* sp., *Schinopsis* sp. (Quebracho), *Castanea* sp., *Quercus* sp., *Rhizophora* sp., *Picea* sp., *Pinus* sp. or *Larix* sp or from other plant sources, such as grape seed extracts, green tea extracts, black tea extracts, white tea, cocoa extracts, wine polyphenols, tannins from fruit or vegetables such as Persimmon or Kaki tannin, grapes, pomegranate, berries, citrus fruits or soy beans, or tannins from herbs and spices such as rosemary. Condensed tannins may also be synthetically prepared by coupling reactions between phenolic compounds. These compounds are known under the general name Syntans.

The topical compositions of the invention can contain one or more of the condensed tannins, which may be fully or partially phosphorylated.

Hydrolysable tannins are complex molecules occurring in natural products, composed of a central nucleus with hydroxybenzoic acids or hydroxycinnamates esterified onto the central nucleus or esterified onto an aromatic hydroxyl function of the molecule. This last type of bond is better known as a depsidic bond. Examples of products containing one or two depsidic bonds are digallic acid and trigallic acid. Examples of these hydroxybenzoic acids are gallic acid and ellagic acid. Examples of hydroxycinnamic acids are caffeic acid, ferulic acid or synaptic acid.

Hydrolysable, naturally occurring tannins all contain such acids or a mixture of these acids esterified on glucose, on glycerol, on quinic acid, on shikimic acid, on a carbohydrate or a sugar in general.

The most abundant central nuclei are glucose such as in tannin from Chinese gallnuts and Aleppo nuts, and quinic acid such as in Tara tannin. The most abundant organic acids esterified onto these central nuclei are gallic acid and/or ellagic acid. Hydrolysable tannins composed with ellagic acid are known as ellagitannins.

Hydrolysable tannins based on glucose and gallic acid are typically composed of gallic acid and its oligomers, monogalloylglucose, di-, tri-, tetra-, penta-, hexa-, hepta-, octa-, nona-, deca-, undeca-, and dodecagalloylglucose, and smaller quantities of ellagitannins. Higher substitutions may also occur, but are rare. They are a mixture of the mentioned compounds in a ratio largely dependent on the plant origin.

Hydrolysable tannins are typically obtained by extraction of plant materials such as Chinese gall nuts, Bengal Kino, Aleppo nuts, Sumac tannin, Turkish tannin, Tara tannin, Acer tannin. Hydrolysable tannins are present in all plants, and thus may also be extracted from other plant sources. Topically acceptable hydrolysable tannin extracts are widely commercially available. Alternatively, hydrolysable tannins may also be composed of dimers and oligomers of hydroxybenzoic acids such as for example the dimeric ester digallic acid, ellagic acid, trigallic acid and higher oligomers. Hydrolysable tannins may also consist of condensed tannins serving as the central nucleus on which gallic acid or ellagic acid is esterified. Combinations of tannins with different properties may be used to improve the performance of the products. Other derivatives found in nature include esters and ethers of gallic acid and/or ellagic acid with simple alcohols such as methanol or ethanol. These may also combine to more complex structures, in the same way as described above. The phosphorylated condensed or hydrolysable tannins may also be dimeric or trimeric phosphates, consisting of one central phosphate group with two or three phenolic compounds attached to it. They may also be diphosphates or triphosphates, containing two or three phosphate groups bond to each other.

It will be understood that, as use herein both in the specification and claims, the term "phosphorylated polyphenol" or "phosphorylated tannin", or the reference to any individual compound, includes not only the phosphorylated base compounds, as discussed above, but also any phosphorylated derivatives and analogues thereof, mixtures thereof, as well as any phosphorylated plant extracts or mixtures thereof.

The phosphorylated polyphenols useful in the invention can be prepared by the steps of reacting a phosphoryl chloride with a polyphenol in aqueous medium using inorganic bases. In a preferred embodiment this aqueous medium is water. The inorganic base can be a metal hydroxide, a carbonate, a phosphate and/or ammonia. Most preferred is sodium hydroxide. The base can be added prior and/or during addition of the phosphorylating agent, i.e. the reagent.

The base is used to increase the pH of the reaction mixture to values between 5 and 13 depending on the acidity of the hydroxyl function. Preferably, the pH of the reaction mixture is kept between 7 and 12.

The phosphoryl chloride preferably is represented by the general formulas:

$$R_nPOX_{3-n} \quad (IV)$$

or $$R_vPX_w \quad (V)$$

wherein n=0, 1 or 2, v+w=3 or 5, X is a chloride, bromide or iodide and R is an alkoxide with an alkyl chain of 1-8 carbon atoms, or O-Phenyl or O-benzyl. In an embodiment according to the invention, the phosphoryl chloride is phosphorous oxychloride (POCl₃).

The phosphoryl chloride that is used as phosphorylating agent preferably is applied in a ratio varying from 0.5 equivalent to over 25 equivalents per mole of phenolic hydroxyl compound, depending on the structure of the phenolic antioxidant, and more specifically on the amount of hydroxyl groups present in the molecule. The degree of phosphorylation can be controlled using high-pressure chromatography for instance.

After the phosphorylation step, the reaction mixture may be acidified. Preferably, a pH of about 2 to about 7 is obtained by the addition of mineral acids.

Preferably the phenolic compounds that constitute the starting material are more complex polyphenolic compounds such as condensed and/or hydrolysable tannins. The product obtained in aqueous solution can be used as such, can be concentrated by distillation or other means known to those skilled to the art and/or can be dried. The phosphorylated product according to the invention may be present as such or in a more or less purified form.

From the broad groups designated above, some specific types of polyphenols are particularly preferred as the starting material for phosphorylation, because of their recognized biological activities and benefit to skin, hair and/or nails. Generally speaking, the more complex polyaromatic polyphenols are preferred over the monoaromatic compounds such as pyrogallol or gallic acid. Flavonoid compounds in particular are widely used for topical application, and confer a broad range of known benefits. In one embodiment, preferred types of flavonoids for use in the present compositions include, but are not limited to, phosphorylated flavanones, chalcones, flavones, isoflavones, flavonols, flavanols, coumarins, chromones, dicoumarols, chromanones, or chromanols, either alone or in combination. In another embodiment, other compounds that are very useful in the compositions of the invention are phosphorylated hydroxystilbenes, such as resveratrol, its isomers and derivatives, also having a wide range of activities.

Without limitation, specific compounds or groups of compounds that may be used in the present compositions are phosphorylated forms of: catechol and derivatives thereof, such as DL-3,4-dihydroxyphenylalanine or DL-DOPA; catecholamines such as 3-hydroxytyramine or dopamine; phloroglucinol; phenolic acids, such as caffeic acid, dihydrocaffeic acid, ferulic acid, protocatechuic acid, chlorogenic acid, isochlorogenic acid, gentisic acid, homogentisic acid, gallic acid, hexahydroxydiphenic acid, ellagic acid, rosmarinic acid or lithospermic acid, and derivatives thereof, such as esters or their heterosides; curcumin; salicylic acid, polyhydroxylated coumarins, polyhydroxylated lignans or neolignans; silymarin, apigenol, luteolol, quercetin, quercetagin, quercetagetin, chrysin, myricetin, rhamnetin, genistein, morin, gossypetin, kaempferol, rutin, naringin, narigenin, hesperitin, hesperidin, diosmin, diosmoside, amentoflavone, fisetin, vitexin, isoliquirtigenin, hesperidin methylchalcone, taxifoliol, silybin, silychristin, silydianin, catechin, epicatechin, gallocatechin, catechin gallate, gallocatechin gallate, epicatechin gallate, epigallocatechin gallate and epigallocatechin; glucogallin; proanthocyanidin; propyl gallate, isoamyloctyl gallate and dodecyl gallate; penta-O-galloyl glucose; tannic acid; various tannins such as gallotannin, ellagitannin; shikimic acid, and resveratrol (3,4',5'-trihydroxystilbene); and any derivatives or analogues of the foregoing compounds. It will be recognized that each of these phosphorylated forms can be used alone, in combination with another phosphorylated polyphenol or an unphosphorylated polyphenol.

It will also be recognized that the useful compounds or groups of compounds can be used in substantially pure form, i.e., at a purity of 80% or greater, or they can be provided as a part of a plant extract. Virtually every plant contains some form of polyphenol, but there are certain plants or plant extracts that are recognized as being particularly rich sources of polyphenols. Examples of plants which may produce extracts useful in the compositions include plants of the genera: *Gingko, Lespedeza, Passiflora, Silybum, Citrus, Hamamelis, Thymus, Chamaemelum, Achillea, Equisetum, Sophora, Fagopyrum, Eucalyptus, Sambucus, Betula, Vitis, Pinus, Crataegus, Quercus, Ratanhia, Lythrum, Acacia, Cupressus, Vaccinium, Ribes, Centaurea, Rosa, Hibiscus, Camellia, Malva, Podophyllum, Schizandra, Gaiacum, Theobroma, Arctostaphylos, Glycine, Cynara, Rosmarinus, Orthosiphon, Solidago, Lithospermum, Curcuma, Aesculus, Melilotus, Ammi, Hieracium, Angelica,* and *Asperula*. In particular, it is well known that particularly rich sources of polyphenols include red wine, grape juice, grape skins, grape seeds, blueberries, persimmon, eucalyptus, cocoa, green tea, black tea, white tea, pomegranate, and Chinese gallnut. Thus, when referring to phosphorylated polyphenols in the present specification and claims, this phrase is intended to cover not only isolated compounds that have been phosphorylated, but also extracts of plant materials containing polyphenols, which extracts have also been subjected to the phosphorylation procedure, thereby phosphorylating the polyphenols contained therein.

As shown in example 5, the phosphorylated compounds so prepared show an enhanced stability in a cosmetic formulation relative to their unmodified counterparts.

The compounds are also useful in achieving delayed release of the active polyphenol molecule on the topical surface to be treated. It is often preferred to have the activity of a topical composition prolonged over a period of time, so that the beneficial effect is extended, and also so that a larger amount of the active component can be delivered in a single dosage. As shown in example 6, the phosphorylated compounds can be dephosphorylated by phosphatases present in the skin, and the dephosphorylated compounds are thus gradually released into the skin, rather than being immediately available as would be typical with the nonphosphorylated version of the same molecule. Thus, the compositions of the invention provide a dual potential benefit: the active compounds contained therein are not readily degraded, and thus can retain more activity between the time of formulation and the time of application, and the delayed release of the active onto the treated surface allows a more effective delivery of that compound.

As shown in example 6, the dephosphorylion with phosphatase leads to restoration of the biological activity.

An additional unexpected advantage is that the phosphorylation of certain polyphenols can result in an increase in their water solubility. This has been particularly demonstrated with resveratrol, which is in its unphosphorylated form relatively water-insoluble. The addition of the relatively polar phosphate groups on the molecule increases its polarity, and thus its solubility in water and polar solvents, as shown in Example 2. Lack of solubility in water can be a severe limitation in formulation, and so phosphorylated polyphenols may be more useful than their unphosphorylated counterparts in formulating compositions for topical application.

The phosphorylated compounds can be formulated into compositions in combination with topically acceptable carriers in much the same manner as their unphosphorylated counterparts. The carriers will be those that are pharmaceutically or cosmetically acceptable, that is, a vehicle, for either pharmaceutical or cosmetic use, intended for application to external body surfaces, such as skin, hair or nails, which vehicle delivers the active components to the intended target and which will not cause harm to the average human or other recipient organisms when applied to the surface intended to be treated. As used herein, "pharmaceutical" or "cosmetic" will be understood to encompass both human and animal, preferably mammalian, pharmaceuticals or cosmetics. with which the active component is compatible, e.g., a gel, a cream, a lotion, an ointment, a mousse, a spray, a solid stick, a powder, a suspension, a dispersion, and the like. Techniques for formulation of various types of vehicles are well known to those skilled in the art, and can be found, for example, in *Chemistry and Technology of the Cosmetics and Toiletries Industry*, Williams and Schmitt, eds., Blackie Academic and Professional, Second Edition, 1996 *Harry's Cosmeticology*, Eighth Edition, M. Reiger, ed. (2000), and *Remington: The Science and Practice of Pharmacy*, Twentieth Edition, A. Gennaro, ed., (2003), the contents of each of these being incorporated herein by reference. The chemical composition of the carrier will vary according to the identity of the active, and the intended final use. However, any typical composition that is useful for topical delivery, for example, aqueous dispersions, anhydrous compositions in liquid, solid or powder form, emulsions (oil or silicone-in-water, water-in-oil or silicone, multiple emulsions, microemulsions, nanoemulsions), can be employed, provided the components are compatible with the active of choice. The compositions can be formulated for application to the skin, for example, skin care products, such as sunscreens, self-tanners, skin moisturizers and conditioners, exfoliators, anti-acne compositions, anti-aging compositions, and the like; or color cosmetics, such as lipstick, lipgloss, foundation, eyeshadow, blush or eyeliner; for application to hair, lashes and/or scalp, for example, mascara, lash primers or coating products, hair growth retarding compositions, hair growth promoting compositions, shampoos, or conditioners; or for application to the nails, for example, nail lacquer, top coats, base coats, ridge fillers, and nail conditioners. Since many of the unphosphorylated forms of these polyphenols have been previously formulated for topical use, it is well within the skill of the art to determine an appropriate formulation for the particular phosphorylated polyphenol of interest. The amounts of phosphorylated polyphenol incorporated into the carrier will vary depending upon the identity of the polyphenol and the intended result, but normally the amount of polyphenol in the composition will be in the range of from about 0.0001 to about 99% by weight of the composition, preferably, about 0.001 to about 50%, more preferably about 0.01 to about 30%, and most preferably about 0.05 to about 10%. When employing polyphenol-containing extracts rather than isolated compounds, incorporated amounts will depend on the polyphenol concentration in the extract, and can be extrapolated from the above guidelines for the polyphenols per se. The composition can also contain other topically useful components which may enhance or complement the activity of the composition. The choice of accompanying ingredients in the composition will also depend upon the intended use of the compositions. Standard topically useful ingredients can be found in, for example, The International Cosmetic Ingredient Dictionary and Handbook, 10th Edition, 2004, the contents of which are incorporated herein by reference. Examples of useful categories of topically acceptable ingredients that may be combined with the phosphorylated phenols include, but are not limited to: fragrances or essential oils; pigments or colorants; formulation aids such as anti-caking agents, anti-foaming agents, fillers and bulking agents, thickeners, gellants, structuring agents and emulsion stabilizers; surfactants and emulsifiers; film-forming agents to enhance adhesion and retention on the intended target; propellants, preservatives and pH adjusters and neutralizing agents.

Particularly preferred for addition to the phosphorylated polyphenol are those ingredients that provide an additional benefit to the keratinous surface to which the composition will be applied, hereinafter referred to as "skin benefit agents". Examples of such skin benefit agents include, but are not limited to, astringents, such as clove oil, menthol, camphor, eucalyptus oil, eugenol, menthyl lactate, witch hazel distillate; antioxidants or free-radical scavengers, such as ascorbic acid, its fatty esters and phosphates, tocopherol and its derivatives, N-acetyl cysteine, sorbic acid and lipoic acid; anti-acne agents, such as salicylic acid and benzoyl peroxide; antimicrobial or antifungal agents such as caprylyl glycol, triclosan, phenoxyethanol, erythromycin, tolnaftate, nystatin or clortrimazole; chelating agents, such as EDTA; topical analgesics, such as benzocaine, lidocaine or procaine; anti-aging/anti-wrinkle agents, such as retinoids or hydroxy acids; skin lightening agents, such as licorice, ascorbyl phosphates, hydroquinone or kojic acid), skin-conditioning agents (e.g., humectants, including miscellaneous and occlusive), antiirritants, such as cola, bisabolol, aloe vera or panthenol, anti-inflammatories, such as hydrocortisone, clobetasol, dexamethasone, prednisone, acetyl salicylic acid, glycyrrhizic acid or glycyrrhetic acid; anti-cellulite agents, such as caffeine and other xanthines; humectants, such as alkylene polyols or hyaluronic acid; emollients, such as oily esters or petrolatum; sun protecting agents (organic or inorganic), such as avobenzone, oxybenzone, octylmethoxycinnamate, titanium dioxide or zinc oxide; exfoliating agents (chemical or physical), such as N-acetyl glucosamine, mannose phosphate, hydroxy acids, lactobionic acid, peach kernels, or sea salts; self-tanning agents, such as dihydroxyacetone; and biologically active peptides, such as palmitoyl pentapeptide or argireline. These supplemental skin benefit agents will be used in the amounts normally known to be effective for that active when used for the intended purpose.

The compositions of the invention have numerous uses. As already noted above, the polyphenols as a group possess a myriad of biological activities, and many types of polyphenols have been reported to possess more than one type of activity. For example, various tannins, particularly flavonoids, have been reported to have activity in the treatment of hypoactive or hyperreactive skin conditions, such as atopic dermatitis, eczema, psoriasis, folliculitis, rosacea, and acne (U.S. Pat. No. 6,180,662,); as free radical scavenger and antioxidants useful in preventing signs of aging (U.S. Pat. Nos. 4,698,360 and 6,437,004,); and as nitric oxide and apoptosis modulators, antineoplasic agents, and inhibitors of oxidative DNA damage (U.S. Pat. No. 6,696,495) Similarly, stilbenes, and particularly resveratrol, have been stated to have activity in inhibiting glycation of dermal proteins (EP 1058864); stimulating collagen synthesis or fibroblast proliferation (U.S. Pat. No. 6,147,121); inhibiting microbial growth (EP 953345); skin lightening (U.S. Pat. No. 6,132, 740); prevention and/or treatment of skin cancer, sunburn, eczema, dermatitis or psoriasis (WO 01/30336); in hair coloring (EP 1013260); and as phytoestrogens (WO 99/04747) The disclosures of all the foregoing patent documents are incorporated herein by reference in their entirety. Thus, it is clear that a large number of polyphenols have significant utility in the regulation of the condition of the keratinous tissues, particularly the skin. The present invention therefore provides a method for regulating the condition of a keratinous tissue, such as skin, hair or nails, which comprises applying to the tissue a composition containing an effective amount of a phosphorylated polyphenol. An effective amount of a phosphorylated polyphenol is an amount of the polyphenol capable of achieving the therapeutic effect intended. This will typically be in the range of the amount used for unphosphorylated polyphenols, and in any event, is readily extrapolated from the ranges for the known compounds.

In the particular application of the present invention, the activity of interest is the ability to regulate skin condition. The citations noted above, as well as many others, illustrate the diversity of effects that the phosphorylated polyphenols can have on the skin. It will be understood, that, as used herein, the term "regulating" skin condition means both the treatment and prevention of skin conditions, in particular, those conditions that represent a pathology, as well as those that, although less serious, may cause discomfort, or present an unattractive or less appealing appearance. Examples of skin conditions that can be treated, ameliorated, reduced or prevented include, but are not limited to, eczema, seborrhea, psoriasis, xerosis, neoplastic growths, dermatitis, folliculitis, rosacea and acne.

In a preferred embodiment, the skin condition to be regulated is one or more of the conditions that may be referred to collectively as the signs of skin aging. The appearance of skin normally changes with age, due to a number of internal factors associated with time. However, the skin can also be prematurely aged by virtue of its overexposure to environmental factors such as sun, pollution, or cigarette smoke. As used herein, the regulation of skin conditions resulting from aging is intended to encompass both the signs of chronoaging as well as photo- or environmentally-induced aging. The manifestations of the aging process are many, and may be both external (i.e., immediately visible) or internal (i.e., not immediately visible to the naked eye). Those skilled in the art will readily recognize the numerous examples of the signs of aging. Such examples include, without limitation, fine lines and wrinkles, deep wrinkles, pitting and bumps, increased pore size, keratoses, skin flakiness or roughness, unevenness or blotching of skin tone, yellowing of the skin, dark undereye shadows or circles, loss of skin elasticity, sagging (including puffiness in the eye area and jowls), elastosis, loss of skin firmness or tightness, hyperpigmentation, age spots and freckles, abnormal differentiation, hyperkeratinization, collagen breakdown, spider veins, or telangiectasia, among others.

Part of the activity observed in regulating skin conditions may be their well-known activity as free radical scavengers or antioxidants. Many environmental agents, such as various dietary elements, pesticides, sunlight, tobacco smoke, air pollutants, anesthetics, and aromatic hydrocarbons, to which modern man is routinely exposed, as well as a variety of endogenous aerobic reactions, can generate highly reactive oxygen species, such as superoxide anion radicals, hydrogen peroxide and hydroxyl ions, as well as singlet oxygen (not strictly speaking a free radical, but included as such herein for convenience). These reactive oxygen species have been implicated in a number of reactions that can cause serious damage to cellular components: for example, oxidizing radicals can attack the bases and sugar molecules of DNA, altering the molecular structure and thereby interfering with biological functions. They may also interact with unsaturated fatty acids in cell membranes, causing lipid peroxidation, which results not only in alteration of the protein:lipid interaction of the membrane, but in the production of breakdown products which can exert a host of undesired effects, such as inhibition of DNA synthesis, adenyl cyclase and glucose-6-phosphate, increase in capillary permeability and inhibition of platelet aggregation. Considerable evidence exists that unchecked free radical reactions have some, if not major, involvement, in a number of disease states, for example, emphysema, inflammation, cancer, atherosclerosis and cataracts. Free radical reactions are also widely considered to have a major contributory effect on the natural aging process, as noted above. Because of the well-known activity of numerous polyphenols as free-radical scavengers and antioxidants, the phosphorylated polyphenols, as their biological equivalents, are expected to have the same utility. Therefore, the present invention also provides a method of reducing or preventing free radical damage which comprises applying to cells at risk of free radical damage, a free radical scavenging-effective amount of at least one phosphorylated polyphenol. This method will be understood to encompass the treatment or prevention of pathological conditions in which a contributory factor is the adverse effect of reactive oxygen species.

In a similar vein, phosphorylated polyphenols can be conveniently employed as preservative antioxidants in food, cosmetics, pharmaceuticals and the like. It is the nature of certain types of formulations, particularly those that may be high in lipid content, to susceptible to spoilage due to the action of oxygen species on their contents. One or more phosphorylated polyphenols can be added to such formulations so as to preserve their components against oxygen damage, and to prevent rancidity. Similarly, due to their antimicrobial activity, they may provide an added preservative effect in the prevention or reduction of contamination due to microbial activity.

The methods of application of the topical compositions of the invention will vary depending upon the identity of the phosphorylated polyphenol and on the intended end use of the composition. In general, for the regulation of various skin conditions, or for the prevention or treatment of conditions associated with oxygen free radicals, compositions can be applied either in advance of the exposure to the potentially damaging factor (e.g., sunlight), or after the exposure for the amelioration of damage that may have occurred as a result of the exposure. Application can continue for as long as the exposure to the noxious stimulus continues, or can be discontinued when relief is obtained. When being used to treat, ameliorate or prevent a more permanent condition, for example, everyday exposure to sun or environmental damage, or for the treatment or prevention of signs associated with chronoaging, the composition is preferably applied chronically, to prevent the occurrence or recurrence of the condition. For this purpose, it is suggested as an example that topical application of the composition, in an amount of from about 0.1 $mg/cm^2$ to 2 $mg/cm^2$ of the keratinous surface to be treated, be performed from about once per week to about 4 or 5 times daily, preferably from about 3 times a week to about 3 times daily, most preferably about once or twice per day. By "chronic" application, it is meant herein that the period of topical application may be over the lifetime of the user, preferably for a period of at least about one month, more preferably from about three months to about twenty years, more preferably from about six months to about ten years, more preferably still from about one year to about five years, thereby resulting in the treatment, amelioration, reduction or prevention of the condition in question.

Other uses for the phosphorylated polyphenols will be readily recognized upon the reading of this specification. The invention is further illustrated by the following non-limiting examples.

EXAMPLES

Example 1

Phosphorylation of Grape Seed Tannin 100.0 g. of grape seed tannin (*TANFOS* 167-134) was dissolved in 300 mL of water at room temperature under nitrogen atmosphere. The solution was brought to a pH of 9 with NaOH 29%, and 26.6 mL phosphorous oxychloride was added to the solution over a period of 1.5 hours. During this addition, more NaOH 29% was added to maintain the pH at 9. After the addition, the reaction mixture was stirred overnight, and analysed by HPLC. The product was then acidified with HCl 25% to a pH of 3.1 and isolated via spray drying to obtain a pink powder.

Example 2

Phosphorylation of Resveratrol

The structure of the compound known as resveratrol (3,4,5-trihydroxystilbene) is as follows:

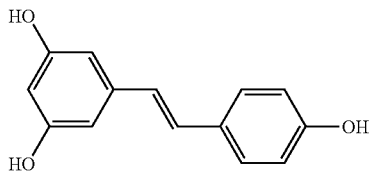 [SMILES: Oc1ccc(/C=C/c2cc(O)cc(O)c2)cc1]

Phosphorylation can be achieved, for example, by the procedure disclosed by Pettit et al., *J. Med. Chem.* 2002, 45, 2534-2542). A solution of resveratrol (25 mmols, 5.7 g) and dimethylaminopyridine (7.5 mmols, 0.93 g) in 100 mL of acetonitrile is cooled under nitrogen up to −10° C. After 10 minutes, CCl4 (375 mmol, 36.2 mL) and DIEA (159 mmols; 27.7 mL) and the mixture maintained under stirring for 30 minutes. Dibenzylphosphite (113 mmols, 25.0 mL) is added and the mixture stirred for an additional 12 hours at room temperature. The course of the reaction is monitored by TLC (Silica F254, eluent ethyl acetate/n-hexane 80/20 v/v). One liter 0.5 M $KH_2PO_4$ is added, and the mixture then extracted with ethyl acetate. The resulting product, tri(dibenzylphosphate) resveratrol is purified by filtration on a silica gel, washing first with a mixture of ethyl acetate/n-hexane (80/20 v/v) to remove any remaining unreacted resveratrol, and then with methanol, to obtain a yellow oil.

To the tri(dibenzylphosphate)resveratrol (12.5 mmol) in 200 mL of anhydrous DCM at 0° C., is added bromomethylsilane (79 mmols, 10.4 mL). After 2 hours, 300 mL of $H_2O$ is added, and the reaction mixture is stirred for 1 hour. The water phase is washed again with ethyl acetate, then lyophilized to obtain an orange oil.

To the product obtained above, solubilized in 400 mL of ethanol, is added $CH_3ONa$ (37 mmol; 2.03 g) and the reaction stirred for 12 hours at room temperature. The ethanol is evaporated in a rotavapor and the residue solubilized in $H_2O$. The water phase is washed with ethyl acetate and lyophilized. The mass spectrum of the white solid obtained thereby shows the presence of resveratrol triphosphate (PM=468.1), with a total yield of >90% with respect to resveratrol.

Example 3

Solubility of Resveratrol Triphosphate

The water solubility of resveratrol is tested at pH 7 in 1 mM potassium phosphate buffer at room temperature. Ten mg of resveratrol (M.W. 228.24) are suspended in 10 ml of buffer. This suspension, corresponding to a concentration of 1 g/l or 4.38 mM, is agitated for 24 hours in a rotary shaker at 25° C. in the dark. The sample is centrifuged at 14,000 rpm for 5 minutes and an OD of 6.26 is determined at 305 nm wavelength at which the $\epsilon$ mM of resveratrol has a value of 28.1. Assuming complete solubility of resveratrol, the OD that should have been obtained is 123.1 (4.38×28.1). With an observed OD of 6.26, the percentage of dissolved resveratrol is 5.1% (6.26×100/123.1) or 5.1 mg/l.

In contrast, the solubility and stability of the resveratrol triphosphate tested under the same conditions, in water of different pH, in the range of 4 to 9, at room temperature. The solubility of the resveratrol triphosphate is observed to be >30% w/v, showing an increase in solubility over unmodified resveratrol. In addition, the resveratrol triphosphate is stable in both solid and water solution form for periods in excess of one year.

Example 4

Dephosphorylation of Resveratrol Triphosphate In Vitro

A phosphorylated resveratrol, and herein designated as resveratrol$^{Pi}$, is evaluated to determine if it is possible to dephosphorylate the molecule, to return it to the active, dephosphorylated state.

A. HPLC Analysis of Resveratrol and Resveratrol$^{Pi}$

The experimental conditions for the HPLC analysis of resveratrol are shown below.

| | |
|---|---|
| Technique: | HPLC-UV |
| Column: | Alltech, Alltima C18 5μ (250 * 4.6 mm) |
| Column temperature: | 30° C. |
| Mobile phases: | A: 0.085% o-phosphoric acid solution |
| | B: Acetonitrile |
| Injection column: | 10 μl |
| Flow rate: | 1 ml/min |
| λ detection: | 310 nm |
| Retention times: | Resveratrol 8.2 minutes |
| | Resveratrol$^{Pi}$ 40.7 minutes |

Gradient:

| Time (min) | Solvent A (%) | Solvent B (%) |
|---|---|---|
| 0 | 98 | 2 |
| 50 | 60 | 40 |
| 55 | 0 | 100 |
| 65 | 0 | 100 |
| 72 | 98 | 2 |
| 85 | 98 | 2 |

The chromatogram of the non-phosphorylated resveratrol is shown in the upper frame in FIG. 1. This is the HPLC profile of the starting material that is the starting material for phosphorylation. Non-phosphorylated resveratrol migrates at about 40.7 minutes and was almost pure with an area percent of 98%. The highly phosphorylated resveratrol is shown in the lower frame of FIG. 1. The main peak at 8.2 minutes is the completely phosphorylated resveratrol in which phosphate groups substitute all three hydroxyl functions. This substitution causes a significant increase in polarity, which is reflected in a dramatic decrease in retention time. Two "impurities" can be detected: two isomers of the diphosphorylated resveratrol ($t_m$ around 14.6 and 16.7 minutes) and of the monophosphorylated resveratrol ($t_m$ around 23.3 and 26.7 minutes). Only very small amounts of non-phosphorylated resveratrol are detected.

B. Enzymatic Dephosphorylation of Resveratrol$^{Pi}$

Phosphorylated resveratrol was incubated in the presence of acid phosphatase from wheat germ (Sigma, P3627 lot 081K7071) in 0.147M $(NH4)_2SO_4$/0.81 mM $MgCl_2$ pH 5.5. The concentration of resveratrol$^{Pi}$ and acid phosphatase was 1.6 mg/ml and 0.056 U/ml respectively. Aliquots were taken at different time intervals and analysed by HPLC (conditions see above).

Results are shown in FIG. 2. Treatment of resveratrol$^{Pi}$ with acid phosphatase resulted in a time dependent formation of resveratrol, while the tri-phosphorylated resveratrol (completely phosphorylated) decreased gradually. Identification of the peaks was confirmed by retention behaviour and UV spectra. The amount of resveratrol diphosphate initially goes up, reaches a maximum around 85 minutes of incubation with acid phosphatase and then decreases progressively. At the start of the incubation with the enzyme the greater part of resveratrol is completely phosphorylated hence the conversion of the tri- to diphosphorylated resveratrol is dominant. This causes a net increase of diphosphorylated resveratrol. At longer incubation times there is less resveratrol triphosphate and thus less conversion to resveratrol diphosphate and the conversion from di- to monophosphorylated resveratrol becomes dominant, which causes an overall decrease in resveratrol diphosphate at longer incubation time (>85 minutes). The incubation time dependent concentration profile of resveratrol monophosphate is similar to the one of the diphosphate. This is consistent with the formation/removal mechanism proposed above, but the maximum concentration of resveratrol monophosphate is now reached at longer incubation times (~300 minutes).

C. Conclusions

In order to increase the stability of resveratrol in formulation the reactive hydroxyl groups of resveratrol were replaced by phosphate groups (~Resveratrol$^{Pi}$). HPLC analysis of the phosphorylated resveratrol shows that the degree of phosphorylation is very high, since only very small amounts of the non-phosphorylated resveratrol are detected. This experiment shows that acid phosphatase from wheat germ is able to replace the phosphate groups of resveratrol$^{Pi}$ by hydroxyl groups and as such converts the phosphorylated resveratrol to the original hydroxyl-containing resveratrol.

Example 5

Visual (Color) Stability of a Cosmetic Formulation Containing Equimolar Levels of Resveratrol Triphosphate or the Unmodified Resveratrol Three base formulas are prepared, the control containing no resveratrol, the other two formulas being identical to the control but for one containing 0.1% unmodified resveratrol, and the other containing 0.2% of phosphorylated resveratrol (Resveratrol$^{Pi}$).

| Material | Weight Percent |
|---|---|
| Sequence 1 | |
| Stearic acid | 2.400 |
| Glyceryl monostearate | 2.200 |
| Butyl paraben | 0.100 |
| Lanolin alcohol/mineral oil/BHT | 9.550 |
| Lanolin alcohol/petrolatum/BHT | 2.000 |
| Sesame Oil | 4.300 |
| Propyl paraben | 0.100 |
| Sequence 2 | |
| Deionized water | 38.630 |
| Triethanolamine | 0.820 |
| Methyl paraben | 0.300 |
| Trisodium EDTA | 0.100 |
| Propylene glycol | 1.300 |
| Sequence 3 | |
| Deionized water | 35.000 |
| Sequence 4 | |
| Propylene glycol | 3.000 |
| Phopshorylated resveratrol | 0.200 |

The color of the control base is white, and with addition of the resveratrols, it takes on a light beige color. Each formulation is observed once a week for a period of four weeks to determine the presence of a color change (indicative of changing color stability), under three different environmental conditions: 50° C., 4° C., and room temperature (RT). The results obtained are as follows:

1 Week Stability
vehicle Control 50-white/4-white/RT-white
0.1% Resveratrol 50-lt beige/4-lt beige/RT-lt beige
0.2% Resveratrol$^{Pi}$ 50-lt beige/4-lt beige/RT-lt beige
2 Week Stability
vehicle Control 50-white/4-white/RT-white
0.1% Resveratrol 50-lt beige/4-lt beige/RT-lt beige
0.2% Resveratrol$^{Pi}$ 50-lt beige/4-lt beige/RT-lt beige
3 Week Stability
vehicle Control 50-white/4-white/RT-white
0.1% Resveratrol 50-lt beige (vsl darker with sl top oxidation)/4-lt beige/RT-lt beige
0.2% Resveratrol$^{Pi}$ 50-lt beige/4-lt beige (vvsl lighter than other stations)/RT-lt beige
4 Week Stability
vehicle Control 50-white/4-white/RT-white
0.1% Resveratrol 50-beige (sl darker than RT with top oxidation)/4-lt beige (sl lighter beige than RT)/RT-lt beige/beige
0.2% Resveratrol$^{Pi}$ 50-lt beige/4-lt beige (vvsl lighter than other stations)/RT-lt beige
sl=slightly, vsl=very slightly, vvsl=very very slightly These results illustrate that at the end of four weeks, the phosphorylated resveratrol shows less color development than the unmodified resveratrol, confirming the enhanced color stability of the phosphorylated material.

Example 6

Dephosphorylation of Resveratrol Triphosphate by Stratum Corneum Cells

A. HPLC analysis of resveratrol and resveratrol$^{Pi}$

The experimental conditions for the HPLC analysis of resveratrol are as described above in Example 4.
Gradient:

| Time (min) | Solvent A (%) | Solvent B (%) |
|---|---|---|
| 0 | 98 | 2 |
| 40 | 68 | 32 |
| 47 | 5 | 95 |
| 57 | 5 | 95 |

-continued

| Time (min) | Solvent A (%) | Solvent B (%) |
|---|---|---|
| 62 | 98 | 2 |
| 75 | 98 | 2 |

A chromatogram of non-phosphorylated resveratrol and of the highly phosphorylated resveratrol prepared by Omnichem is shown in FIG. 1. See analysis of peaks is as stated above in Example 4.

B. Enzymatic Dephosphorylation of Resveratrol$^{Pi}$

D-squame tape strippings were collected on the inner lower arm of one panelist. Layer 13 and 14 were pooled and put in a test tube and extracted with 700 μl of 100 mM phtallic acid and 0.25% Triton-X100 at pH 5.6 for 90 minutes at room temperature with gentle shaking. The extractable fraction was transferred to another vial and mixed with resveratrol$^{Pi}$ stock-solution. The concentration of resveratrol$^{Pi}$ during the incubation was 0.22 mg/ml or 0.47 mM. At various incubation time points a 25 μl aliquot of the incubation mixture was diluted in 25 μl 10 mM o-phosphoric acid and 50 μl of MeOH and injected onto the HPLC system.

Results are shown in FIG. 3. Incubation of resveratrol$^{Pi}$ with the extractable fraction of SC D-squame tape strippings resulted in a time dependent formation of resveratrol ($r=0.99$, $N=15$, $p<1*10^{-6}$), while the tri-phosphorylated resveratrol (completely phosphorylated) decreased gradually ($r=-0.69$, $N=15$, $p=0.005$).

Time dependent formation of mono-phosphorylated resveratrol is also observed ($r=0.98$, $N=15$, $p<1*10^{-6}$). Overall amounts of the di-phosphorylated form of resveratrol did not change significantly as a function of time ($r=-0.27$, $N=15$, $p=0.33$), which indicates that the formation of di-phosphorylated resveratrol (from completely phosphorylated resveratrol) is equally fast as the conversion of di- to mono-phosphorylated resveratrol.

C. Conclusions

The present experiment attempted to show that the phosphorylated resveratrol would be dephosphorylated by enzymes present in the skin. Enzymatic dephosphorylation of phosphorylated resveratrol e.g. by in situ acid phosphatase activity in the skin would reconstitute the original resveratrol with a concomitant increase in biological activity. The results shown in FIG. 3 indicate that acid phosphatase present on the skin and sampled via D-squame tape strippings is able to replace phosphate groups on resveratrol$^{Pi}$ by hydroxyl groups. This results in a time dependent formation of resveratrol and a corresponding decrease of resveratrol$^{Pi}$, thereby supporting the concept of delayed release of the active resveratrol molecule, or any phosphorylated polyphenol, by the action of stratum corneum enzymes when the phosphorylated polyphenol is applied to the skin.

Example 6

In Vitro Antioxidant Activity after Dephosphorylation of Resveratrol Triphosphate Phosphorylated resveratrol (resveratrol$^{Pi}$) (0.256 mM) is incubated with various concentrations of acid phosphatase from wheat germ for 6 hours at 37° C. in 20 mM citric acid buffer at pH 5 with 0.05% Triton-X100. The concentration of acid phosphatase ranges from 0.063 to 63 mU/ml. Since the conversion of phosphorylated resveratrol will depend on the concentration of acid phosphatase, it is expected that at higher acid phosphatase concentrations increasing amounts of dephosphorylated resveratrol will be present.

A test to determine the efficiency of antioxidants in aqueous systems is set up using 2,2'-azobis(2-amidinopropane).2HCl (AAPH at 2 mM) as a free radical initiator. The production of conjugated diene hydroperoxide generated through the oxidation of linoleic acid (at 0.16 mM) in an aqueous system of 50 mM phosphate buffer at pH 7.4 at 30° C. is monitored at 234 nm. The antioxidant efficiency is measured by its ability to quench free radicals and hence slow down or stop oxidation of linoleic acid.

The results are shown in FIG. 4. The x-axis in this figure corresponds to the amount of acid phosphatase that is incubated with a fixed concentration of resveratrol$^{Pi}$. Increasing concentration of acid phosphatase thus corresponds to increasing amounts of dephosphorylated resveratrol. This results in a dose dependent increase of the antioxidant activity.

In summary these data show that enzymatic dephosphorylation of phosphorylated resveratrol results in restoration of activity measured as the in vitro antioxidant activity against the AAPH induced oxidation of linoleic acid.

What is claimed is:

1. A topical composition for application to a keratinous tissue, comprising at least one water soluble phosphorylated stilbene selected from the group consisting of resveratrol monophosphate, resveratrol diphosphate, resveratrol triphosphate, mixtures thereof, and metal salts thereof, in combination with a cosmetically or pharmaceutically acceptable carrier.

2. The composition of claim 1 in which the phosphorylated stilbene is a metal salt of resveratrol monophosphate, resveratrol diphosphate, resveratrol triphosphate or mixtures thereof.

3. The composition of claim 1 in which the phosphorylated stilbene is resveratrol triphosphate.

4. The composition of claim 1 which comprises at least one skin benefit agent selected from the group consisting of astringents, antioxidants, free radical scavengers, anti-acne agents, antimicrobial agents, antifungal agents, chelating agents, anti-aging agents, anti-wrinkle agents, analgesics, skin lightening agents, skin conditioning agents, anti-irritants, anti-inflammatories, anti-cellulite agents, humectants, emollients, organic sunscreens, inorganic sun protecting agents, chemical exfoliating agents, physical exfoliating agent, self-tanning agents, biologically active peptides; and mixtures thereof.

5. The topical composition according to claim 1, wherein said water soluble phosphorylated stilbene is selected from the group consisting of resveratrol diphosphate, resveratrol triphosphate, and metal salts thereof.

6. A method of regulating skin condition comprising applying to the skin of a subject in need thereof the topical composition according to claim 1.

7. The method of claim 6 in which the skin condition to be treated is selected from the group consisting of eczema, seborrhea, psoriasis, xerosis, neoplastic growths, dermatitis, folliculitis, rosacea and acne.

8. The method of claim 6 in which the skin condition to be treated is one or more signs of skin aging.

9. The method of claim 6 in which the phosphorylated stilbene is resveratrol triphosphate.

10. A method of regulating the effects of reactive oxygen species on a cell of a keratinous tissue, said method comprises applying to the cell of a subject in need thereof the topical composition according to claim 1.

* * * * *